United States Patent [19]

Thomas et al.

[11] Patent Number: 5,830,738
[45] Date of Patent: Nov. 3, 1998

[54] EXTRACTION OF PIGMENT FROM PLANT MATERIAL

[75] Inventors: Ronald L. Thomas, Clemson, S.C.; Kathryn Diane Deibler, Shalimar, Fla.; Charles Rice Barmore, Moore, S.C.

[73] Assignee: Clemson University, Clemson, S.C.

[21] Appl. No.: 658,144

[22] Filed: Jun. 4, 1996

[51] Int. Cl.$^6$ ...................................................... C12N 9/42
[52] U.S. Cl. ............................................................ 435/209
[58] Field of Search .................................. 435/209, 267; 426/425, 428

[56] References Cited

U.S. PATENT DOCUMENTS

| | | | |
|---|---|---|---|
| 5,019,405 | 5/1991 | Sapers | 426/250 |
| 5,130,237 | 7/1992 | Thomas et al. | 435/96 |
| 5,472,859 | 12/1995 | Brown, Jr. et al. | 435/101 |

OTHER PUBLICATIONS

Casey et al. Advanced Practical Organic Chemistry, 1990, (Chapman Hall: New York).

Kanner et al. "Carotenoids extraction from orange peel by treatments with enyzmes and d–limonene" Int. Fruchtsaft–Union (1984) 18, pp. 219–225.

Brady et al. General Chemistry Principles and Structure, 1978, (John Wiley: New York).

Webster's II New Riverside University Dictionary 1994 (Houghton Mifflin:Boston), p. 1167.

Tengerdy et al. "Plant processing by simulatneous lactic acid fermentation and enzyme hydrolysis", Appl. Biochem. Biotech. (1992) 34/35: 309–316.

George A. Spanos, Hao Chen and Steven J. Schwartz, Supercritical $CO_2$ Extraction of β–Carotene from Sweet Potatoes, 1993, Journal of Food Science pp. 817–820, vol. 58 No. 4.

C.A. Sims, M.O. Balaban, and R.F. Matthews, Optimization of Carrot Juice Color and Cloud Stability, 1993 Journal of Food Science pp. 1129–1131 vol. 58(5).

Maria Tsimidou and Euphoria Tsatsaroni, Stability of Saffron Pigments in Aqueous Extracts, 1993, Journal of Food Science vol. 58 No. 3 pp. 1073–1075.

C.E. Fabre, A.L. Santerre, M.O. Loret, R. Baberian, A. Pareilleux, G. Goma, and P.J. Blanc, Production and Food Applications of the Red Pigments of Monascus ruber, 1993, Journal of Food Science vol. 58(5) pp. 1099–1102.

G.M. Sapers, Color Characteristics and Stability of Non-bleeding Cocktail Cherries Dyed with Carotenoid Pigments, 1994, Journal of Food Science vol. 59 No. 1 pp. 135–138.

C.M. Hong, W.L. Wendorff, and R.L. Bradley, Jr., Factors Affecting Light–Induced Pink Discoloration of Annatto–Colored Chesse, 1995, Journal of Food Science vol. 60 No. 1 pp. 94–97.

Primary Examiner—Jon P. Weber
Assistant Examiner—Susan Hanley
Attorney, Agent, or Firm—Dority & Manning, P.A.

[57] ABSTRACT

The present invention is directed to a process for extracting pigments, namely carotenoids, from plant material. The process includes the step of combining shredded plant material with an enzyme. The enzyme breaks down the plants cellular walls releasing the carotenoids contained within the plant cells. The enzyme added to the plant material can be pectinase, cellulase, hemicellulase, or mixtures thereof.

27 Claims, 1 Drawing Sheet

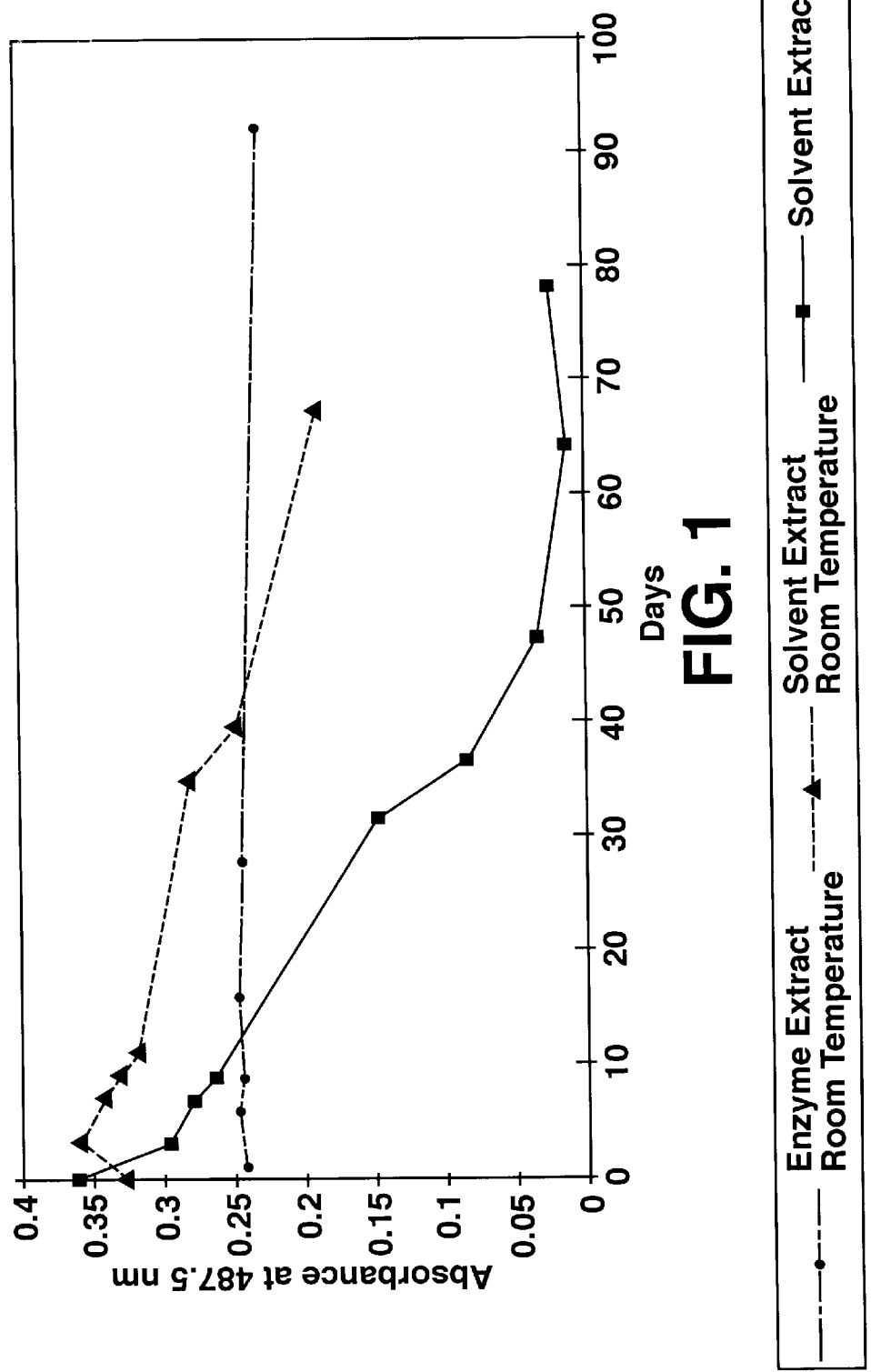
Figure 1. A comparison of the degradation of absorbance at 487.5 nm of the enzyme extract from orange peels held at room temperature and exposed to light with the degradation of the solvent extract held at room temperature and at 40°C.

EXTRACTION OF PIGMENT FROM PLANT MATERIAL

BACKGROUND OF THE INVENTION

The present invention generally relates to a process for extracting pigments from plant materials and, more particularly, to a process for extracting carotenoids from plant material using enzymes.

Carotenoids generally refer to a class of labile, easily oxidizable, yellow, orange, red, or purple pigments that are widely distributed in plants. All photosynthetic organisms contain one or more carotenoid pigments. Carotenoids are typically found in the chloroplast of plant cells in close association with chlorophyll. Due to their chemical structure, the carotenoids are capable of absorbing photons of light at wave lengths between about 300 nm to about 700 nm. It is believed that once light is absorbed, the carotenoids are then capable of transferring the energy from the high energy photons to chlorophyll for carrying out photosynthesis, a process by which plants manufacture carbohydrates by absorbing light.

Carotenoids can be found in leaves, stems, vegetables, fruits and flowers of plants. Concentrated amounts of carotenoid pigments are known to exist in carrots, sweet potatoes, orange juices and orange peels, which accounts for the characteristic orange color of these plants. Carotenoid pigments are also responsible for the color of most autumn leaves after the chlorophyll has broken down. Besides plants, carotenoids exist in the skins and skeletons of some animals. For instance, carotenoids are responsible for the pink color of flamingo feathers.

Chemically, carotenoids are comprised of a string of isoprene units (structural unit containing five carbon atoms), resulting in a conjugated carbon double bond chain. By definition, a carotenoid molecule contains a chain of eight isoprene units. The electrons in the conjugated carbon double bonds are easily excitable while the conjugation permits the absorption of light energy. Depending upon the carotenoid molecule, other chemical groups, such as carbonyl groups, hydroxyl groups, and epoxide groups, can be attached to the conjugated carbon chain. The specific wave length of light absorbed by a particular carotenoid molecule is determined by the number, type and position of these other chemical groups, the number and position of the carbon double bonds, and the stearic configuration of the molecule.

In nature, carotenoids typically exist in association with stabilizing agents, which prevent the molecule from oxidizing or otherwise degrading. For instance, carotenoids can be associated with such stabilizing agents as proteins, fatty acids and sugars. A protein-carotenoid complex is referred to as a chromoprotein. Besides protecting the carotenoids, these stabilizing agents can also affect the solubility of carotenoids, which are typically water insoluble.

Because most carotenoids exhibit bright colors, these pigments have much potential use as a coloring agent. Carotenoid pigments have been found to be particularly useful as food colorants or food dyes. Being derived from a natural source, carotenoid pigments are considered safe for human consumption. In fact, many carotenoids are vitamin A precursors and are effective antioxidants. It is believed that some carotenoid pigments when ingested serve to prevent some forms of cancer.

In the past, others have attempted to extract carotenoid pigments from plant matter for such commercial uses. Unfortunately, however, past practices have had only limited success, producing unstable extracts with limited use as a food dye.

For instance, attempts have been made to extract carotenoids from plants using harsh solvents. Such solvents have included benzene, petroleum ether, carbon disulfide, chloroform, ethanol, methanol, and acetone. To extract the carotenoids, the plant material is soaked in the solvent at room temperature. After soaking the plant material in the solvent, the carotenoids are then separated from the rest of the plant matter.

In an article entitled "Supercritical $CO_2$ Extraction of $\beta$-Carotene from Sweet Potatoes," appearing in *The Journal of Food Science* by Spanos et al., a process for extracting the carotenoid, $\beta$-carotene, from sweet potatoes using supercritical carbon dioxide is disclosed. As discussed in the article, sweet potato tissue was first dried either in a freeze drier or in a forced air oven. The dried material was ground with a mortar and pestle and then fed to a continuous supercritical fluid extraction apparatus for extracting the carotenoids.

In the above prior art systems, however, the resulting extracted carotenoid pigments, and especially the color of the pigments, are very unstable. It is believed that during the above-described solvent extractions and supercritical carbon dioxide extractions, the pigments are released or separated from the stabilizing agents that the carotenoids are associated with in nature. Without the stabilizing agents, the carotenoids degrade when exposed to light, heat or oxygen. For instance, light exposure will cause extensive oxidation of the carotenoids adversely effecting their color. Consequently, the resulting extracts have a very short shelf life, are typically kept in organic solvents and must always be protected from light, heat and oxygen.

Enzymes have been used in the past for various purposes. For instance, in an article entitled "Optimization of Carrot Juice Color and Cloud Stability," by Sims et al., which was published in *The Journal of Food Science*, the enzymes pectinase and hemicellulase were added to milled and heated carrots for the production of vegetable juice. The enzymes were added to the carrots in order to assess the effects of the enzyme mixture on yield, color and cloud stability of the resulting carrot juice. It was found that the enzyme preparation improved juice color but had no effect on juice yield or the overall turbidity of the juice.

Enzymes, however, have not been used for the purpose of extracting plant pigments. Further, from the following detailed description it will be apparent that other various features, aspects and advantages of the present invention remain absent from the prior art.

SUMMARY OF THE INVENTION

The present invention recognizes and addresses the foregoing disadvantages, and others of prior art constructions and methods.

Accordingly, it is an object of the present invention to provide a method of extracting carotenoid pigments from plant matter.

It is another object of the present invention to provide a method of extracting carotenoid pigments from plant material using enzymes.

Another object of the present invention is to provide a method of extracting carotenoids that remain bound in their stable and natural state.

It is still another object of the present invention to provide a method of extracting carotenoid pigments that can be used as food dyes.

It is another object of the present invention to provide a method of extracting carotenoid pigments from plant material by breaking down the cell walls of plant cells for releasing any carotenoids contained therein.

These and other objects of the present invention are achieved by providing a process for the extraction of carotenoids from plant material. In view of the deficiencies and drawbacks of prior art methods, the present invention is directed to an improved method of extracting carotenoid pigments from plant material. Instead of using harsh solvents and process conditions, the present invention is generally directed to using enzymes for breaking down the outer cell structure of plant cells in order to release the carotenoids contained therein. It is believed that through this process, the carotenoids are extracted in their bound natural state, providing a highly stable product.

The process includes the steps of contacting plant material with an enzyme. The enzyme breaks down the cellular walls of the plant cells for releasing the carotenoids contained therein. Although not necessary, the carotenoids can then be separated from the rest of the plant material.

Plant material that is particularly well suited for use in the process of the present invention includes carrots, sweet potatoes, and flabedo orange peels. The plant material can be shredded prior to being contacted with the enzyme. Also, in order to facilitate mixing with the enzyme, the shredded plant material can be combined into an aqueous suspension.

The enzyme used in the present invention can be, for example, pectinase, cellulase, hemicellulase or mixtures thereof. In one embodiment, pectinase and cellulase can be added together to the plant material. Pectinase can be added in an amount up to about 25% by weight based on the weight of the plant material, while the cellulase can be added in an amount up to about 15% by weight based on the weight of the plant material.

The process can further include the steps of filtering the plant material once the enzymes have been added to produce a filtrate comprising water soluble carotenoids and a filter residue. The filter residue, if desired, can be washed with a solvent in order to dissolve any water insoluble carotenoids and to produce a carotenoid and solvent solution. Water can then be added to the solvent and carotenoid solution in an amount sufficient to precipitate the carotenoids. The solvent can then be evaporated from the solution containing the precipitated carotenoids.

Other objects, features and aspects of the present invention are discussed in greater detail below, or may be obvious from the description, or may be learned through practice of the invention.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figure, in which:

Specifically, FIG. 1 represents a comparison of the degradation of absorbance at 487.5 nm of the enzyme extract of the present invention from orange peels held at room temperature and exposed to light with the degradation of a solvent extract held at room temperature and at 40° C.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

In general, the present invention relates to a process for extracting pigments, namely carotenoids, from plant materials using enzymes. The carotenoids are extracted from the plant material in their bound natural state. More particularly, the carotenoids are extracted in association with stabilizing agents such as proteins, fatty acids and sugars. As used herein, the term, "stabilizing agent," refers to a chemical compound bound, such as for example through covalent bonds, to a carotenoid, which inhibits the carotenoid from degrading when exposed to, for instance, light, oxygen or heat. By being extracted in association with stabilizing agents, the carotenoids produced according to the present invention are much more stable than carotenoids extracted by prior art methods.

Carotenoids extracted according to the present invention are useful in many different applications. For instance, the carotenoids can be used as color-stable food dyes. Being extracted without the use of hazardous solvents, the carotenoids are considered completely safe for human consumption when incorporated into food products. Besides food dyes, the carotenoids can also be used in pharmaceuticals. Particularly, many carotenoids are Vitamin A precursors and are effective antioxidants.

As stated above, according to the process of the present invention, enzymes are used to extract the carotenoids from plant materials. The enzymes used in the process breakdown the cell structures of plant cells, thereby releasing the carotenoids contained within the cells. Specifically, the enzymes used in the process are capable of catalyzing the degradation of pectin and cellulose, the primary building blocks of plant cellular walls. Particular enzymes that can be used in the present invention include pectinase, cellulase, and hemicellulase.

It is believed that the enzymes used in the process of the present invention break down the outer structures of the plant cells without adversely interfering with the carotenoids contained within the cells. Thus, the carotenoids extracted remain in tact in their bound natural state in association with stabilizing agents. Due to the stabilizing agents, the extracted carotenoids remain stable after being separated from the plant material. Importantly, the carotenoids extracted according to the process of the present invention will retain their characteristic bright colors for extended periods of time.

Generally speaking, any plant tissue or material containing pigments can be used in the process of the present invention. Preferably, the plant material contains a concentrated amount of carotenoids. For example, plants well suited for use in the process of the present invention include carrots, sweet potatoes and flabedo orange peels.

Prior to being contacted with an enzyme, the plant material can first be shredded or milled down to a small particle size. The smaller the particle size of the plant material, the more surface area is created for contact with the enzymes. In order to shred the plant material, any suitable milling equipment can be used including any suitable food processing machinery.

In one embodiment, after being shredded, the plant material is blended with a liquid to form a suspension. The liquid, which can be for instance distilled water, preferably does not react with the plant material. In order to form a suspension, the liquid and the plant material are thoroughly mixed which further reduces the size of the plant material. A mechanical mixer or blender can be used. The formed suspension facilitates later mixing with the enzyme.

The enzymes can be added to the plant material either during or after formation of the suspension. The enzymes are added in an amount sufficient to break down the cellular walls of the plant cells for releasing the carotenoids contained therein.

As stated above, particular enzymes that may be used in the process of the present invention include pectinase, cellulase or hemicellulase. These enzymes can be added either alone or in combination with the others. Of the above enzymes, perhaps pectinase is the most effective at breaking down the cellular structures. It is believed that when the enzymes are added as a mixture, pectinase breaks down the plant cells while cellulase and hemicellulase further reduce the particle size and viscosity of the resulting plant matter.

In general, pectinase can be added to the plant material in an amount up to about 25% by weight based on the weight of the plant material. When cellulase and/or hemicellulase are added in combination with pectinase, the cellulase and/or hemicellulase can be added in an amount up to about 15% by weight based on the weight of the plant material. In most applications, the enzymes added in an amount of about 5% by weight based on the weight of the plant material will be sufficient to release the carotenoids contained within the plant material. Adding the enzymes in excess, however, has been found to cause no adverse affects. Consequently, the enzymes can be added in much greater amounts than as described above if desired.

In one preferred embodiment, a mixture of pectinase and cellulase are added to the plant material. Pectinase can be added in an amount of about 25% by weight based on the weight of plant tissue, while the cellulase can be added in an amount of about 13% by weight based on the weight of the plant tissue contained within the suspension.

The enzymes, pectinase, cellulase or hemicellulase are commercially available as a liquid concentrate or as a dry powder. Either form may be used in the process of the present invention. Pectinase, cellulase and hemicellulase are commercially available from Genencor, Inc. of San Francisco, Calif.

In general, it has been found that the reaction that occurs between the plant material and the enzymes proceeds at a suitable rate at room temperature. If desired, the temperature can be increased or decreased in order to increase or decrease the rate of reaction. Temperatures that will cause the plant material or the carotenoids to degrade should be avoided.

Once the enzymes have been added to the plant material and after thorough mixing, the suspension will contain plant cell fragments, water soluble carotenoids and lipid soluble carotenoids. Although it will depend on the particular plant being used in the process, generally speaking the lipid soluble carotenoids will be much more concentrated in the suspension than the water soluble carotenoids.

Once the enzymes have been mixed into the suspension, the carotenoids can be commercially used in combination with the plant material or can be further processed if desired. In one embodiment, the suspension can be filtered through a sedimentary filter such as a CELITE bed (which is primarily composed of diatomaceous earth) in order to isolate the water soluble carotenoids. Other filters, such as membrane filters, paper filters and fabric filters may be used also. Once the suspension is filtered through a suitable filter, the resulting filtrate contains the water soluble carotenoids while the filter residue contains plant cell fragments and the lipid soluble carotenoids. The filtrate containing the water soluble carotenoids can be used as desired. In general, the filtrate will primarily contain xanthophylls, which are a particular class of carotenoids.

The filter residue containing the lipid soluble carotenoids, similar to the filtrate, need not be further refined but may be used as desired and incorporated into a product or process requiring the use of a pigment. In some applications, however, it is preferred to separate the lipid soluble carotenoids from the plant material.

In one embodiment, the filter residue can be washed with a mild solvent in order to dissolve and separate the lipid soluble carotenoids from the plant cell fragments. The solvent preferably is a "nondisassociating" solvent which, as used herein, refers to a solvent that dissolves the lipid soluble carotenoids without breaking apart the carotenoid-stabilizing agent complex. The solvent can be, for instance, an alcohol, such as ethanol or propylene glycol. Preferably, the solvent chosen is non-toxic.

After washing with a solvent, the remaining plant matter can be discarded leaving behind a solvent and carotenoid solution. Since the lipid soluble carotenoids are water insoluble, water can be added to the solvent and carotenoid solution in order to precipitate the carotenoids. Once precipitated, the carotenoids can be separated from the solvent by filtration or in any other suitable manner.

When an alcohol or other volatile liquid is used as a solvent, the resulting solution can be heated under a vacuum in order to evaporate the solvent. The lipid soluble carotenoids thus remain as a precipitate in an aqueous solution. The carotenoids can be separated and dried for use in various applications, such as in a food dye or in a pharmaceutical. The evaporated solvent, on the other hand, can be condensed, collected and reused in the process.

It is believed that the process of the present invention can be used to extract any desired carotenoid from all types of plant material. Representative carotenoids that can be recovered from plant material according to the process of the present invention include, without limitation, xanthophyll, cryptoxanthin, β-carotene, β-citraurin, zeaxanthin, violaxanthin, α-crocin, lycopene, bixin, curcumin, capsanthin, capsorubin and canthaxanthin.

The present invention may be better understood with reference to the following examples.

PIGMENT EXTRACTION TESTS

Carotenoids were extracted from navel orange peels, carrots and sweet potatoes according to the following procedure.

The navel orange peels, carrots and sweet potatoes were first chopped by hand into about one square centimeter pieces. When using orange peels, the inside albedo surface and the peel oils were first abraded off using a wire screen. After being chopped, the plant material was homogenized in deionized distilled water by a POLYTRON or WARING blender, which further reduced the particle size of the plant material and increased the surface area for reaction. The enzymes, pectinase and cellulase, were added to the plant and water suspension and stirred with a magnetic stirring bar for approximately 24 hours at ambient temperature.

A CELITE bed was formed in a BUCHNER funnel. In each example, the suspension was vacuum filtered through the CELITE bed. The resulting filtrate in each trial was a tea-like color and contained the water soluble carotenoids present in the plant material.

The filter residue from the bed was washed with 95% ethanol. The initial washings, which primarily contained oils, were discarded. Ethanol was added to the residue until the original color of the CELITE bed had nearly returned.

hours of overhead laboratory light a day and held in duplicate at 4° C., 25° C. and 40° C. Other samples were kept in darkness by being wrapped in aluminum foil and similarly held in duplicate at 4° C., 25° C. and 40° C.

During a 134 day period, absorbance readings were taken of the samples using a spectrophotometer. Absorbance was measured at 487.5 nm where carotenoids typically exhibit absorbance.

The data was averaged and the following results were obtained:

TABLE 2

STABILITY TESTS

| Ex. No. | Test Cond | Absorbance | | | | | | | | | | Total Percent Degradation |
|---|---|---|---|---|---|---|---|---|---|---|---|---|
| | | Day 1 | Day 6 | Day 9 | Day 16 | Day 28 | Day 93 | Day 95 | Day 99 | Day 129 | Day 134 | |
| 7 | 4° C. Dark | 0.239 | 0.246 | 0.242 | 0.232 | 0.231 | 0.237 | — | — | — | — | 0.8 |
| 8 | 4° C. Light | 0.239 | 0.248 | 0.243 | 0.230 | 0.230 | 0.235 | 0.232 | — | — | — | 2.9 |
| 9 | 25° C. Dark | 0.239 | 0.244 | 0.241 | 0.239 | 0.239 | 0.232 | — | 0.226 | — | — | 5.4 |
| 10 | 25° C. Light | 0.239 | 0.244 | 0.240 | 0.244 | 0.241 | 0.224 | 0.211 | 0.215 | 0.189 | 0.182 | 23.8 |
| 11 | 40° C. Dark | 0.239 | 0.258 | 0.242 | 0.243 | 0.239 | — | — | — | — | — | 0.0 |
| 12 | 40° C. Light | 0.239 | 0.258 | 0.236 | 0.242 | 0.238 | — | — | — | — | — | 0.0 |

Water was then added to the ethanol solution that had been filtered through the CELITE bed. Water was added until a carotenoid precipitate formed. The ethanol was then removed and recovered using a rotary vacuum evaporator at 50° C., leaving the lipid soluble carotenoids suspended in a small amount of water. The lipid soluble extract was bright orange in each test and visually appeared to be much more intense than the water soluble extract.

The following table lists all of the samples tested.

TABLE 1

Extraction Tests

| | Plant Type | Weight of Plant Material (g) | Water Added (ml) | Pectinase Added (ml) | Cellulase Added (g) |
|---|---|---|---|---|---|
| Example No. 1 | Orange Peel | 32 | 100 | 10 | 5 |
| Example No. 2 | Orange Peel | 64 | 150 | 20 | 10 |
| Example No. 3 | Orange Peel | 115 | 175 | 25 | 15 |
| Example No. 4 | Orange Peel | 63 | 150 | 20 | 10 |
| Example No. 5 | Sweet Potato | 309 | 400 | 15 | 15 |
| Example No. 6 | Carrots | 323 | 300 | 15 | 15 |

STABILITY TESTS

The following tests were performed to measure the stability of the lipid soluble pigments extracted as described above.

Specifically, the lipid soluble carotenoids extracted from orange peels in Example No. 4 above were incorporated into soybean oil to simulate a fat based food system. The carotenoid extract was added to the soybean oil at 20% volume of the resulting solution.

Ten (10) mL samples of solution were placed in clear glass viles. Tests were conducted to determine the effect of light and temperature on the stability of the samples. Specifically, some of the samples were exposed to 8 to 10

In order to compare the stability of carotenoids extracted according to the present invention with carotenoids extracted using a solvent, crystallized β-carotene extracted using a solvent was similarly tested. The extracted β-carotene was obtained from Sigma Chemical Company in St. Louis, Mo.

Samples of the β-carotene extract were incorporated into soybean oil and into sunflower oil and diluted to obtain absorbance in the same range as was obtained for the enzyme extract samples. The oil solutions were prepared in the same manner as the enzyme extract samples. Some of the solutions were held at 25° C. and exposed to 8 to 10 hours of overhead laboratory light a day, while other samples were held at 40° C. also being exposed to 8 to 10 hours of overhead laboratory light a day. Absorbance readings were taken at 487.5 nm periodically. FIG. 1 is a graphical representation of a comparison of the degradation of absorbance at 487.5 nm of the enzyme extract from orange peels held at room temperature and exposed to light with the degradation of the solvent extracted β-carotene held at room temperature and held at 40° C.

As shown in the figure, the enzyme extract showed superior stability to the solvent extract. The enzyme extract only degraded by approximately 6% after 93 days. The solvent extracted β-carotene held at the same conditions, on the other hand, degraded by 55% after just 82 days. The solvent extracted β-carotene held at 40° C. degraded even more during the same period of time.

YIELD TESTS

The following tests were performed in order to compare the amount of carotenoids extracted according to the process of the present invention versus the amount of carotenoids extracted using a solvent extraction technique.

Carotenoids were extracted from orange peels, carrots and sweet potatoes using the same procedure as described above with respect to Examples 1 through 6. During the process, 25 grams of the chopped plant material was dried in a vacuum oven at 60° C. for 24 hours and weighed. This data was used in the calculation of carotenoid yield per dry weight of the sample.

The enzyme extracted pigments were transferred to reagent grade hexane for the purpose of analysis. The hexane solution was washed with a 10% aqueous solution of sodium chloride and the water phase was discarded. The hexane solution was then washed three times with deionized distilled water, discarding the aqueous phases. The carotenoids in the hexane were dried over anhydrous sodium sulfate in a dark refrigerator at 4° C. for 30 minutes.

Carotenoids were also extracted from orange peels, carrots and sweet potatoes using a solvent extraction procedure. Specifically, a 50 gram sample of a plant material and water suspension was blended with 100 mL of distilled acetone for 3 minutes. The acetone solution was filtered under suction through speed 1 Watman filter paper. The residue was blended with approximately 200 mL with an acetone/hexane ether solution present at a one-to-one ratio. The solution was again filtered under suction. Deionized distilled water was added to the filtrate in a separatory funnel and the aqueous phase was discarded. The hexane solution was then washed with 10% sodium chloride to break emulsions. The solution was washed three more times with deionized distilled water and the aqueous phase was again discarded. The extracted carotenoids in hexane were dried over anhydrous sodium sulfate in a refrigerator at 4° C. for 30 minutes.

Approximate yields of the samples were calculated using the following formula:

$\mu$g carotenoid/g sample=$(A_{487.5})$ (D) (105/181) (light path (cm)) (sample weight(g))

wherein:

$A_{487.5}$=the absorbance of the solution at 487.5 nm

D=the dilution factor based on 100 mL of solvent solution

All yield extractions were conducted in triplicate and the average absorbance was used for yield calculations. The following results were obtained:

TABLE 3

YIELD TESTS

|  | $\mu$g carotenoids/ g wet weight | | $\mu$g carotenoids/ g dry weight | |
| --- | --- | --- | --- | --- |
|  | Enzyme Extract | Solvent Extract | Enzyme Extract | Solvent Extract |
| Orange Peel | 15.65 | 8.54 | 97.19 | 55.66 |
| Carrot | 60.70 | 165.06 | 519.77 | 1538.18 |
| Sweet Potato | 77.90 | 145.49 | 328.83 | 637.69 |

As shown above, with respect to orange peels, the enzyme extraction method of the present invention produced a higher pigment yield. For carrots and sweet potatoes, on the other hand, the above described solvent extraction method produced a higher yield. During testing, it was noticed that some pigment residue remained in the CELITE bed during the enzyme extraction. Therefore, actual yields would be higher had a greater volume of ethanol been used to wash the bed.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A process for extracting carotenoids from pigmented plant material wherein said carotenoids are extracted in their bound natural state in association with stabilizing agents selected from the group consisting of proteins, carbohydrates and lipids, for producing a light and temperature stable extract product, said process consisting essentially of the steps of:

a) providing pigmented plant material having plant cells comprising cell walls and containing carotenoids, wherein said carotenoids exist in said plant cells in a bound natural state in association with stabilizing agents which inhibit degradation of said carotenoids when exposed to light;

b) reacting said pigmented plant material with an enzyme added in an amount sufficient to break down the cell walls of said plant cells for releasing said carotenoids contained therein, said enzyme comprising pectinase, cellulase, hemicellulase or mixtures thereof, said enzyme releasing said carotenoids from said stabilizing agents; and c) collecting said naturally bound carotenoids as an extract product for direct use as a coloring agent.

2. The process as defined in claim 1, further comprising the step of shredding said plant material.

3. The process as defined in claim 2, further comprising the step of suspending said shredded plant material in an aqueous solution.

4. The process as defined in claim 1, wherein said enzyme comprises a mixture of pectinase and cellulase, said pectinase being added in an amount up to about 25% by weight based on the weight of said plant material, said cellulase being added in an amount up to about 15% by weight based on the weight of said plant material.

5. The process as defined in claim 1, wherein said plant material is a material selected from the group consisting of carrots, sweet potatoes, orange peels and mixtures thereof.

6. The process as defined in claim 1, further comprising the step of separating said naturally bound carotenoids from said plant material without separating said carotenoids from said stabilizing agents.

7. The process as defined in claim 1 further comprising the step of incorporating said coloring agent into a food product.

8. The process as defined in claim 6, wherein said naturally bound carotenoids are separated from said plant material by filtering said plant material to produce a filtrate comprising water soluble carotenoids in association with said stabilizing agents and a filter residue comprising lipid soluble carotenoids in association with said stabilizing agents.

9. The process as defined in claim 8, further comprising the step of washing said filter residue with a solvent that does not separate said lipid soluble carotenoids from said stabilizing agents, said solvent dissolving said lipid soluble carotenoids contained therein to form a solution comprising a complex of said lipid soluble carotenoids and said stabilizing agents.

10. The process as defined in claim 9, wherein said solvent is an alcohol.

11. The process as defined in claim 10, wherein said alcohol is selected from the group consisting of propylene glycol and ethanol.

12. The process as defined in claim 9, further comprising the step of adding water to said solution comprising said complex of lipid soluble carotenoids and stabilizing agents in an amount sufficient to precipitate said complex of lipid soluble carotenoids and stabilizing agents.

13. The process as defined in claim 12, further comprising the step of evaporating said solvent from said precipitate comprising said complex of lipid soluble carotenoids and stabilizing agents.

14. A process for extracting carotenoids from pigmented plant material wherein said carotenoids are extracted in their bound natural state in association with stabilizing agents selected from the group consisting of proteins, carbohydrates and lipids, for producing a light and temperature stable extract product, said process consisting essentially of the steps of:

a) providing pigmented plant material having plant cells comprising cell walls and containing carotenoids, wherein said carotenoids exist in said plant cells in a bound natural state in association with stabilizing agents which inhibit degradation of said carotenoids when exposed to light;

b) reacting said pigmented plant material with an enzyme added in an amount sufficient to break down the cell walls of said plant cells for releasing said carotenoids contained therein, said enzyme comprising pectinase, said enzyme releasing said carotenoids from said plant cells without separating said carotenoids from said stabilizing agents; and (c) separating said naturally bound carotenoids from said plant material as an extract product for direct use as a coloring agent.

15. The process as defined in claim 14, wherein said pectinase is added to said plant material in an amount up to about 25% by weight based on the weight of said plant material.

16. The process as defined in claim 14, wherein said enzyme further comprises cellulase, hemicellulase or mixtures thereof.

17. The process as defined in claim 14, wherein said providing pigmented plant material comprises the steps of shredding said plant material and placing said shredded plant material in an aqueous suspension.

18. The process as defined in claim 14, wherein said separating comprises filtering said plant material of step b) through a filter to recover a filtrate comprising water soluble carotenoids in association with said stabilizing agents and a filter residue comprising lipid soluble carotenoids in association with said stabilizing agents.

19. The process as defined in claim 18, wherein said solvent comprises an alcohol.

20. The process as defined in claim 18, wherein said filter is a solid phase filter.

21. The process as defined in claim 18, further comprising the step of washing said filter residue with a solvent that does not separate said lipid soluble carotenoids from said stabilizing agents, said solvent dissolving said lipid soluble carotenoids contained therein to form a solution comprising a complex of said lipid soluble carotenoids and said stabilizing agents.

22. The process as defined in claim 21, wherein said solvent is an alcohol.

23. The process as defined in claim 22, wherein said alcohol is selected from the group consisting of propylene glycol and ethanol.

24. The process as defined in claim 21, further comprising the step of adding water to said solution comprising said complex of lipid soluble carotenoids and stabilizing agents in an amount sufficient to precipitate said complex of lipid soluble carotenoids and stabilizing agents.

25. A process for coloring a food product comprising the steps of:

a) providing pigmented plant material having plant cells comprising cell walls and containing carotenoids, wherein said carotenoids exist in said plant cells in a bound natural state in association with stabilizing agents which inhibit degradation of said carotenoids when exposed to light, said stabilizing agents selected from the group consisting of proteins, carbohydrates and lipids;

b) reacting said pigmented plant material with an enzyme added in an amount sufficient to break down the cell walls of said plant cells for releasing said carotenoids contained therein, said enzyme comprising pectinase, cellulase, hemicellulase or mixtures thereof, said enzyme releasing said carotenoids from said plant cells without separating said carotenoids from said stabilizing agents;

c) collecting said naturally bound carotenoids as an extract product for direct use as a coloring agent; and d) incorporating said naturally bound carotenoids into a food product in an amount sufficient to colorize said food product.

26. The process as defined in claim 25, wherein said enzyme comprises pectinase, said pectinase being added in an amount up to about 25% by weight based on the weight of said plant material.

27. The process as defined in claim 26, wherein said enzyme further comprises cellulase, said cellulase being added to said plant material in an amount up to about 15% by weight based on weight of said plant material.

* * * * *